United States Patent [19]

Mandai et al.

[11] Patent Number: 5,600,047
[45] Date of Patent: Feb. 4, 1997

[54] PROCESS FOR PRODUCING OPTICALLY ACTIVE OLEFIN

[75] Inventors: Tadakatsu Mandai, Okayama; Jiro Tsuji, Sanyo-cho; Manzo Shiono, Okayama, all of Japan

[73] Assignee: Kuraray Co., Ltd., Okayama-ken, Japan

[21] Appl. No.: 459,637

[22] Filed: Jun. 2, 1995

Related U.S. Application Data

[63] Continuation of Ser. No. 45,950, Apr. 14, 1993, abandoned.

[30] Foreign Application Priority Data

Apr. 14, 1992 [JP] Japan .................................. 4-121182
Jul. 8, 1992 [JP] Japan .................................. 4-205938

[51] Int. Cl.$^6$ ................ C07C 1/20; C07C 1/32
[52] U.S. Cl. .......................... 585/357; 585/361
[58] Field of Search .................. 552/540, 544, 552/546, 547, 548, 552; 585/357, 361, 376

[56] References Cited

U.S. PATENT DOCUMENTS

| | | | |
|---|---|---|---|
| 4,051,157 | 9/1977 | Trest et al. | 552/552 |
| 4,419,287 | 12/1983 | Dauben et al. | 552/552 |

FOREIGN PATENT DOCUMENTS

WO9100271 1/1991 WIPO.

OTHER PUBLICATIONS

Mandai et al., The Journal of Organic Chemistry, "A Novel Method for Stereospecific Generation for Either C-20 Epimer in Steroid Side Chains by Palladium–Catalyzed Hydrogenolysis of C-20 Allylic Cabonates", vol. 57, pp. 6090–6092, 1992.
Shimizu et al. Organic Synthesis Chemistry, vol. 49, No. 6 (1991) pp. 526–540 (including English summary).
Calverley, Tetrahedron, vol. 43, No. 20, pp. 4609–4619 (1987).
Tsuji et al., Tetrahedron Letters, No. 7, pp. 613–616 (1979).
Tsuji et al., Synthesis, pp. 623–627 (1986).
Tsuji et al., Chemistry Letters, pp. 1017–1020 (1984).
Tsuji et al., Bull. Chem. Soc. Japan, vol. 62, No. 10, pp. 3132–3137 (1989).
Sekimov et al., J. Org. Chem. U.S.S.R., vol. 19, No. 9(1), 1983, pp. 1621–1624.
Mandai et al., Tetrahedron, vol. 49, No. 25, 1993, pp. 5483–5493.
Fiaud et al., J. Org. Chem., vol. 52, No. 10, 1987, pp. 1907–1911.

Primary Examiner—Charles T. Jordan
Assistant Examiner—John R. Hardee
Attorney, Agent, or Firm—Wenderoth, Lind & Ponack

[57] ABSTRACT

A process for producing an optically active olefin represented by a formula

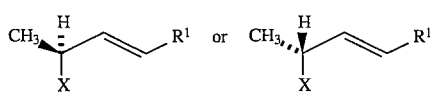

wherein $R^1$ represents an organic group and X represents a polycyclic carbon ring group, by reacting a corresponding optically active ester derivative represented by a formula

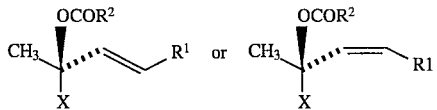

wherein $R^1$ and X are as defined above and R represents a hydrogen atom, an alkoxy group, an alkenyloxy group or a substituted or unsubstituted aralkyloxy group, with formic acid or a salt thereof in the presence of a catalyst comprising a palladium salt and a tertiary phosphine.

Said process makes it possible to produce, at a high yield at a high selectivity, an optically active olefin which has a physiological activity and is useful as a medicine or is useful as an intermediate for the synthesis of physiologically active steroids. Further, said process uses no harmful reagent such as mercury or the like. Thus, it is advantageous as an industrial process.

11 Claims, No Drawings

PROCESS FOR PRODUCING OPTICALLY ACTIVE OLEFIN

This application is a continuation of now abandoned application, Ser. No. 08/045,950, filed Apr. 14, 1993.

The present invention relates to a process for producing an optically active olefin. More particularly, the present invention relates to a process for producing an optically active olefin having a ring structure represented by a hydroindene skeleton, a decalin skeleton or a steroid skeleton, stereospecifically from a corresponding optically active ester derivative. The optically active olefin produced by the present process has a physiological activity by itself and is useful as a medicine or as an intermediate for synthesis of physiologically active substances, particularly steroids.

In steroid synthesis, efforts have been made to control the steric configuration of steroid side chain. As a result, for example, as optically active steroids which have a double bond at the 22-position and whose 20-position is optically active, various compounds have been made known. As such optically active steroids, there can be mentioned, for example, 24-epi-1,25-dihydroxyvitamin $D_2$ and 22,23-dehydro-1,24-dihydroxyvitamin $D_3$ which are under development as a medicine for osteoporosis having a low side effect, as well as 20-epi-22,23-dehydro-24,26,27-trihomovitamin $D_3$ whose 20-position has a steric configuration reverse to that of natural steroids and which is expected as a medicine for psoriasis, dysimmunity, malignant tumor, etc. According to Bulletin of Chemical Society of Japan, Vol. 62, p.3132 (1989), these steroids can be synthesized by reacting an aldehyde derivative such as Diels-Alder adduct between 1α,3β-diacetoxypregna-5,7-diene-20S-carbaldehyde (an ergosterol derivative) and 4-phenyl-1,2,4-triazoline-3,5-dione, 5,6-trans-1α,3β-bis(t-butyldimethylsilyloxy)-9,10-seco-pregna-5,7,10(19)-triene-20R-carbaldehyde (an ergocalciferol derivative) or the like, with a sulfone derivative such as 3-(tetrahydropyran-2-yl)oxy-2,3-dimethylbutyl phenyl sulfone or the like in the presence of a base to form a corresponding 22-hydroxy-23-sulfone derivative and then subjecting the 22-hydroxy-23-sulfone derivative to reduction using a sodium-mercury amalgam.

The above synthesis process, however, is not suitable for industrial application because it uses highly toxic mercury as a reagent. Asteroid whose 20-position has a steric configuration reverse to that of natural steroids can be obtained from the above-mentioned aldehyde derivative whose 20-position has an R steric configuration. According to PCT International Publication No. WO91/00271 and Tetrahedron, Vol., 43, p.4609 (1987), said aldehyde derivative can be obtained by epimerizing a 20S-aldehyde derivative obtained from a natural steroid, to form a mixture of a 20S-aldehyde derivative and a 20R-aldehyde derivative and then subjecting the mixture to liquid chromatography to separate the two isomers from each other. This process, however, employs a complex procedure and is unsuitable for industrial production of the above 20R-aldehyde derivative.

Hence, it is needed to develop a process capable of producing asteroid having an optically active side chain, industrially at a high yield at a high selectivity.

Meanwhile, it is known that an olefin can be obtained regioselectively by reducing straight-chain or branched-chain allyl compounds with formic acid in the presence of a catalyst comprising a palladium salt and a trialkylphosphine or a triarylphosphine, particularly a catalyst comprising a palladium salt and tributylphosphine [Tetrahedron Letters, No. 7, PP-613–616 (1979); Synthesis, 1986, pp. 623–627; Chemistry Letters, pp. 1017–1020 (1984); and Organic Synthesis Chemistry, Vol. 49 No. 6 (1991) pp. 526–540].

In these documents, however, only acyclic or monocyclic allylic esters of relatively low molecular weight are reported and no mention is made on the optical activity. In the cases of such open-chain olefins as mentioned in the above documents, the above reaction shows no stereopeficity.

The present inventors have found that when an optically active ester derivative having a particular ring structure represented by an hydroindene skeleton, a decalin skeleton or asteroid skeleton is reacted with formic acid or a salt thereof in the presence of a palladium salt/tertiary phosphine catalyst, the reaction proceeds highly stereospecifically, whereby a corresponding optically active olefin can be produced at a high yield and, as a result, an optically active olefin, which is steroid having an optically active side chain or an intermediate for synthesis thereof, can be produced industrially at a high yield and a high selectivity.

According to one aspect of the present invention, there is provided a process for producing an optically active olefin represented by general formula (Ia)

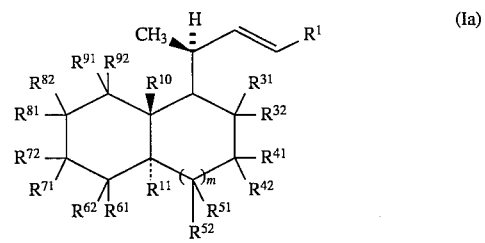

wherein $R^1$ represents an organic group;

$R^{10}$ represents a lower alkyl group;

$R^{11}$ represents a hydrogen atom or a lower alkyl group;

each of $R^{31}$, $R^{32}$, $R^{41}$, $R^{42}$, $R^{51}$, $R^{52}$, $R^{61}$, $R^{62}$, $R^{71}$, $R^{72}$, $R^{81}$, $R^{82}$, $R^{91}$ and $R^{92}$ represents a hydrogen atom, a hydroxyl group which may be optionally protected, or an organic group, or each one pair of the substituents on two adjacent carbon atoms, i.e. ($R^{31}$ or $R^{32}$) and ($R^{41}$ or $R^{42}$), ($R^{41}$ or $R^{42}$) and ($R^{51}$ or $R^{52}$), ($R^{51}$ or $R^{52}$) and $R^{11}$, $R^{11}$ and ($R^{61}$ or $R^{62}$), ($R^{61}$ or $R^{62}$) and ($R^{71}$ or $R^{72}$), ($R^{71}$ or $R^{72}$) and ($R^{81}$ or $R^{82}$), and ($R^{81}$ or $R^{82}$) and ($R^{91}$ or $R^{92}$), may be bonded to each other to form an additional carbon-to-carbon bond, or one pair of the substituents on the same carbon atom, i.e. $R^{31}$ and $R^{32}$, $R^{41}$ and $R^{42}$, $R^{51}$ and $R^{52}$, $R^{61}$ and $R^{62}$, $R^{71}$ and $R^{72}$, $R^{81}$ $R^{82}$, $R^{91}$ and $R^{92}$, may be bonded to each other to form an oxo group which may be optionally protected or a methylene group which may be optionally substituted, or $R^{61}$, $R^{62}$, $R^{71}$ and $R^{72}$ may form an additional ring together with the carbon atoms to which they are bonded; and m is 0 or 1, which process comprises reacting an optically active ester derivative represented by general formula (IIa)

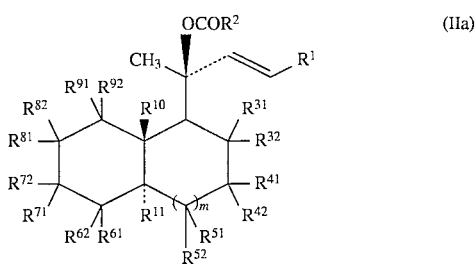

wherein $R^1$, $R^{10}$, $R^{11}$, $R^{31}$, $R^{32}$, $R^{41}$, $R^{42}$, $R^{51}$, $R^{52}$, $R^{61}$, $R^{62}$, $R^{71}$, $R^{72}$, $R^{81}$, $R^{82}$, $R^{91}$, $R^{92}$ and m are as defined above and $R^2$ represents a hydrogen atom, an alkoxy group, an alkenyloxy group or a substituted or unsubstituted aralkyloxy group, with formic acid or a salt thereof in the presence of a catalyst comprising a palladium salt and a tertiary phosphine.

According to another aspect of the present invention, there is provided a process for producing an optically active olefin represented by general formula (Ib)

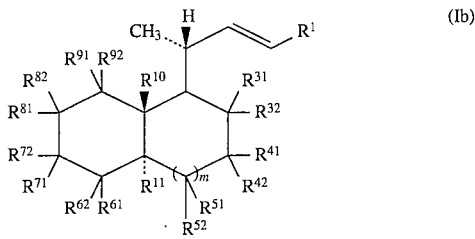

wherein $R^1$, $R^{10}$, $R^{11}$, $R^{31}$, $R^{32}$, $R^{41}$, $R^{42}$, $R^{51}$, $R^{52}$, $R^{61}$, $R^{62}$, $R^{71}$, $R^{72}$, $R^{81}$, $R^{82}$, $R^{91}$, $R^{92}$ and m are as defined above, which process comprises reacting an optically active ester derivative represented by general formula (IIb)

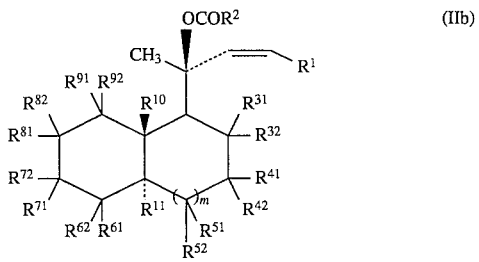

wherein $R^1$, $R^2$, $R^{10}$, $R^{11}$, $R^{31}$, $R^{32}$, $R^{41}$, $R^{42}$, $R^{51}$, $R^{52}$, $R^{61}$, $R^{62}$, $R^{71}$, $R^{72}$, $R^{81}$, $R^{82}$, $R^{91}$, $R^{92}$ and m are as defined above, with formic acid or a salt thereof in the presence of a catalyst comprising a palladium salt and a tertiary phosphine.

The processes provided by the present invention are hereinafter described in detail.

In the present invention, the term "lower" refers to that any group or compound prefixed with the term has 6 or less, preferably 4 or less carbon atoms.

In the general formulas (Ia), (Ib), (IIa) and (IIb), the "organic group" represented by $R^1$ is not particularly restricted unless it has a functional group (e.g. an allyl ester group) capable of becoming a substrate for palladium-catalyzed reaction with formic acid, and can be selected from a wide range of organic groups. However, there can be mentioned, in particular, straight-chain, branched-chain or alicyclic saturated or unsaturated hydrocarbon groups which may have substituents optionally. Examples of such hydrocarbon groups include alkyl groups (particularly those of 1–10 carbon atoms) such as ethyl, propyl, 2-methylpropyl, 3-methylbutan-2-yl, cyclopropylmethyl, 3-methylbutyl, 3-ethylpentyl and the like; and alkenyl groups (particularly those of 2–10 carbon atoms) such as 3-methyl-1-butenyl, 3-ethyl-1-pentenyl, 4-methyl-1-pentenyl, 5-methyl-1,3-hexadienyl and the like. Each of these hydrocarbon groups may be optionally substituted by at least one, preferably 1–6, more preferably 1–2 substituents selected from, for example, a hydroxyl group which may be optionally protected, an oxo group which may be optionally protected, a carboxyl group which may be optionally protected, a halogen atom, etc.

Of the above groups as $R^1$, preferable are those groups which form side chains in the D ring of steroid, for example, straight-chain or branched chain alkyl groups which may each be optionally substituted by 1–2 groups selected from the group consisting of a hydroxyl group which may be optionally protected, an oxo group which may be optionally protected, a carboxyl group which may be optionally protected and a cycloalkyl group.

Herein, the protective group for hydroxyl group in "a hydroxyl group which may be optionally protected", can be an ordinary protective group which can be easily eliminated by an ordinary deprotection means such as hydrolysis, hydrogenolysis or the like. As such a protective group, there can be mentioned, for example, acyl groups such as formyl, acetyl, propionyl, butyryl, isobutyryl, valeryl, isovaleryl, pivaloyl, caproyl, benzoyl, trifluoroacetyl and the like; alkoxycarbonyl groups such as methoxycarbonyl, ethoxycarbonyl, propoxycarbonyl, allyloxycarbonyl, benzyloxycarbonyl and the like; trisubstituted silyl groups such as trimethylsilyl, triethylsilyl, triisopropylsilyl, tert-butyldimethylsilyl, tertbutyldiphenylsilyl and the like; 1-alkoxyalkyl groups such as methoxymethyl, methoxyethoxymethyl, 1-ethoxyethyl, 1-methoxy-1-methylethyl and the like; and 2-oxacycloalkyl groups such as tetrahydrofuranyl, tetrahydropyranyl and the like. When there are two hydroxyl groups adjacent to each other, these adjacent hydroxyl groups may be protected in the form of an acetal with an aldehyde or a ketone.

As the protective group for oxo group in "an oxo group which may be optionally protected", there can be mentioned, for example, acyclic ketals such as dimethylketal, diethylketal, dibenzylketal and the like; cyclic ketals such as ethyleneketal, bromomethylethyleneketal, o-nitrobenzylethyleneketal, trimethyleneketal, 2-methylenetrimethyleneketal, 2,2-dibromotrimethyleneketal, 2,2-dimethyltrimethyleneketal and the like; acyclic thioketals such as dimethylthioketal, diethylthioketal, and the like; and cyclic thioketals such as ethylenethioketal, trimethylenethioketal and the like.

As the protected carboxyl group in "a carboxyl group which may be optionally protected", there can be mentioned, for example, lower alkoxycarbonyl groups such as methoxycarbonyl, ethoxycarbonyl, propoxycarbonyl, isopropoxycarbonyl, butoxycarbonyl, sec-butoxycarbonyl, t-butoxycarbonyl and the like; and aralkyloxycarbonyl groups such as benzyloxycarbonyl, p-methoxybenzyloxycarbonyl and the like.

As preferable examples of the organic group represented by $R^1$, there can be mentioned the followings:

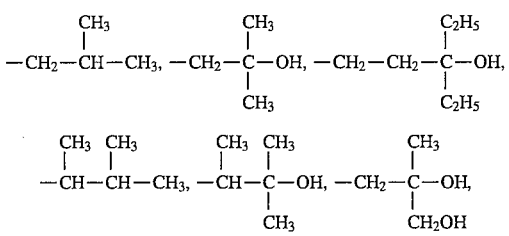

-continued

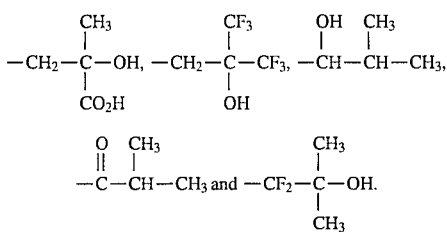

In the above, the hydroxyl group, the oxo group and the carboxyl group may be protected as mentioned above.

The "alkoxy group" and "alkenyloxy group" represented by $R^2$ can be straight-chain or branched-chain and each is preferably a lower group of generally 6 or less carbon atoms. As the alkoxy group, there can be mentioned lower alkoxy groups such as methoxy, ethoxy, propoxy, isopropoxy, butoxy, sec-butoxy, tert-butoxy, hexyloxy and the like. As the alkenyloxy group, there can be mentioned lower alkenyloxy groups such as 3-butenyloxy and the like. The "aralkyloxy" group refers to an aryl-substituted alkoxy group whose alkoxy portion has the same definition as above. The aryl portion, which is preferably a phenyl group, may be optionally substituted by, for example, halogen atom(s), nitro group(s), lower alkyl group(s) (e.g. methyl), lower alkoxy group(s) (e.g. methoxy), etc. Examples of such a substituted or unsubstituted aralkyloxy group are benzyloxy, p-methoxybenzyloxy, p-chlorobenzyloxy and phenethyloxy.

Preferable as $R^2$ is a lower alkoxy group.

The "lower alkyl group" represented by each of R and R can also be straight-chain or branched-chain and includes, for example, methyl, ethyl, propyl, isopropyl, butyl, sec-butyl and tert-butyl. Of these, methyl and ethyl are preferable.

The "organic group" represented by each of $R^{31}$, $R^{32}$, $R^{41}$, $R^{42}$, $R^{51}$, $R^{52}$, $R^{61}$, $R^{62}$, $R^{71}$, $R^{72}$, $R^{81}$, $R^{82}$, $R^{91}$ and $R^{92}$ is not particularly restricted unless it has a functional group capable of becoming a substrate for palladium-catalyzed reaction with formic acid, for example, a functional group such as allyl ester or the like, and can be a straight-chain, branched-chain or cyclic saturated or unsaturated hydrocarbon group which may have a substituent optionally.

Such as hydrocarbon group includes, for example, alkyl groups such as methyl, ethyl, propyl, isopropyl, butyl, sec-butyl, tert-butyl and the like; alkenyl groups such as vinyl, propenyl, 1-butenyl and the like; cycloalkyl groups such as cyclopropyl, cyclopentyl, cyclohexyl and the like; cycloalkylidenealkyl groups such as 2-(2-methylenecyclohexylidene)ethyl and the like; cycloalkenylalkenyl groups such as 2-(2-methyl-1-cyclohexenyl)ethenyl and the like; cycloalkenyl groups such as cyclopentenyl, cyclohexenyl and the like; aryl groups such as phenyl, tolyl and the like; and aralkyl groups such as benzyl, phenethyl and the like.

These hydrocarbon groups may be optionally substituted by, for example, a hydroxyl group which may be optionally protected, an oxo group which may be optionally protected, a carboxyl group which may be optionally protected, a cyano group, an unsubstituted or mono- or disubstituted amino group (e.g. amino, methylamino, dimethylamino, acetylamino, benzyloxycarbonylaimino, t-butoxycarbonylamino, benzoylamino, p-toluenesulfonylamino), a halogen atom, or the like.

Each one pair of the substituents on two adjacent carbon atoms, i.e. ($R^{31}$ or $R^{32}$) and ($R^{41}$ or $R^{42}$), ($R^{41}$ or $R^{42}$) and ($R^{51}$ or $R^{52}$), ($R^{51}$ or $R^{52}$) and $R^{11}$, $R^{11}$ and ($R^{61}$ or $R^{62}$), ($R^{61}$ or $R^{62}$) and ($R^{71}$ or $R^{72}$), ($R^{71}$ or $R^{72}$) and ($R^{81}$ or $R^{82}$), and ($R^{81}$ or $R^{82}$) and ($R^{91}$ or $R^{92}$), may be bonded to each other to form an additional carbon-to-carbon bond; however, the two substituents on the same carbon atom cannot form respective additional carbon-to-carbon bonds simultaneously.

Each one pair of the substituents on the same carbon atom, i.e. $R^{31}$ and $R^{32}$, $R^{41}$ and $R^{42}$, $R^{51}$ and $R^{52}$, $R^{61}$ and $R^{62}$, $R^{71}$ and $R^{72}$, $R^{81}$ and $R^{82}$, and $R^{91}$ and $R^{92}$, may be bonded to each other to form an oxo group which may be optionally protected or a methylene group which may be optionally substituted. The "methylene group which may be optionally substituted", includes a group represented by a formula

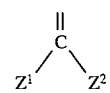

wherein each of $Z^1$ and $Z^2$ represents a hydrogen atom or an organic group mentioned for $R^{31}$ to $R^{91}$ and one of $Z^1$ and $Z^2$ is preferably a hydrogen atom. Preferable examples of such a methylene group are

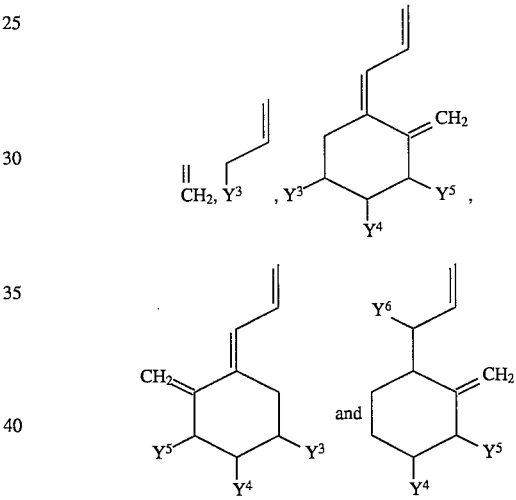

wherein $Y^3$ represents a hydroxyl group which may be optionally protected;

$Y^4$ represents a hydrogen atom, a fluorine atom or a lower alkoxy group which may be substituted by a hydroxyl group which may be optionally protected;

$Y^5$ represents a hydrogen atom or a hydroxyl group which may be optionally protected; and $Y^6$ represents a lower alkoxy group.

$R^{61}$, $R^{62}$, $R^{71}$ $R^{71}$ and may form an additional ring together with the carbon atoms to which they are bonded. The ring may be a monocyclic or polycyclic saturated or unsaturated ring. There can be mentioned, for example, rings of cyclohexane skeleton or decalin skeleton. The ring is preferably the A and B rings portion of steroid.

As the compound constituting the ring structure of formula (IIa) or (IIb), there can be mentioned compounds having at least the C and D rings portion of steroid skeleton, for example, compounds having asteroid skeleton such as androstane skeleton, estran skeleton, seco-androstan skeleton or the like, norsteroid compounds having a skeleton corresponding to the B, C and D rings portion of steroid skeleton, homosteroid compounds having asteroid skeleton whose D ring portion is a 6-membered ring, and compounds having a hydroindene skeleton corresponding to the C and D ring portions of steroid skeleton. These compounds may have double bonds which do not take part in the reaction with formic acid or a salt thereof, at any site and may further have any substituents which do not take part in said reaction. As such substituents, there can be mentioned, for example, a hydroxyl group, halogen atoms, a protected hydroxyl group, an alkyl group which may have a substituent, an alkenyl group which may have a substituent, and an aryl group which may have a substituent.

Preferable examples of the portion of formula (IIa) or (IIb), represented by a formula

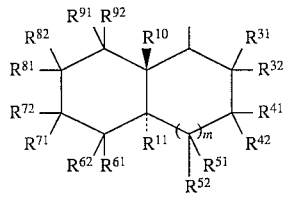

are as follows.

(1) A formula

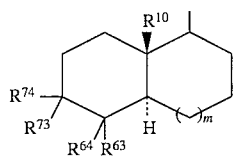

wherein one of $R^{63}$, $R^{64}$, $R^{73}$ and $R^{74}$ represents a hydroxyl group which may be optionally protected or a group of formula (a)

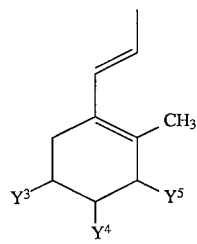

(a)

($Y^3$ represents a hydroxyl group which may be optionally protected; $Y^4$ represents a hydrogen atom, a fluorine atom or a lower alkoxy group which may be substituted by a hydroxyl group which may be optionally protected; and $Y^5$ represents a hydrogen atom or a hydroxyl group which may be optionally protected), and each of the remaining groups is a hydrogen atom or the remaining two groups on two adjacent carbon atoms are bonded to each other to form an additional carbon-to-carbon bond, or $R^{63}$ and $R^{64}$ are bonded to each other to form an oxo group which may be optionally protected or a group represented by formula (b), (c), (d) or (e)

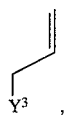

(b)

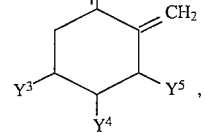

(c)

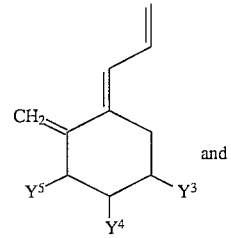

(d)

and

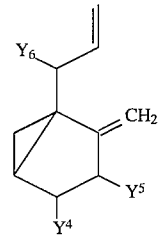

(e)

($Y^3$, $Y^4$ and $Y^5$, are as defined above and $Y^6$ represents a lower alkoxy group) and $R^{73}$ and $R^{74}$ each represent a hydrogen atom, or $R^{63}$, $R^{64}$, $R^{73}$ $R^{74}$ and constitute the A and B rings portion of steroid together with the carbon atoms to which they are bonded; and $R^2$, $R^{10}$ and m are as defined above.

(2) A formula

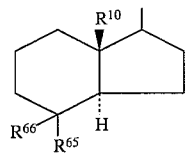

wherein one of $R^{65}$ and $R^{66}$ is a hydroxyl group which may be optionally protected and the other is a hydrogen atom, or $R^{65}$ and $R^{66}$ are bonded to each other to form an oxo group which may be protected or a group represented by formula (c), (d), (e) mentioned above; and $R^2$ and $R^{10}$ are as defined above.

(3) A formula

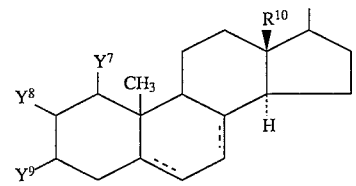

wherein $Y^7$ and $Y^9$ each represent a hydrogen atom or a hydroxyl group which may be optionally protected;

$Y^8$ represents a hydrogen atom, a fluorine atom or a lower alkoxy group which may be substituted by a hydroxyl group which may be optionally protected; and --- represents a single or double bond; and
R² and R¹⁰ are as defined above.

Preferable example of the optically active ester derivative of formula (IIa) is a compound represented by formula (IIa-1), (IIa-2) or (IIa-3):

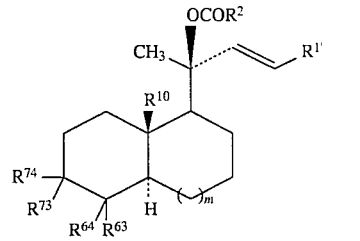
(IIa-1)

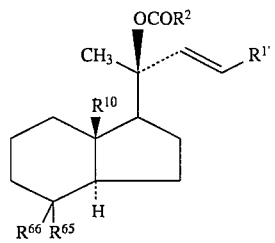
(IIa-2)

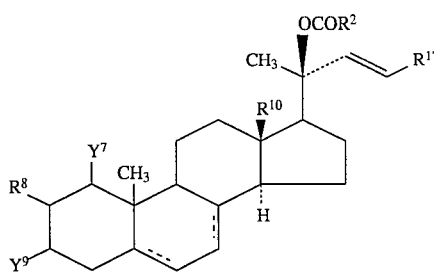
(IIa-3)

wherein R¹' represents a straight-chain or branched chain alkyl group which may be optionally substituted by one or two groups selected from the group consisting of a hydroxyl group which may be optionally protected, an oxo group which may be optionally protected, a carboxyl group which may be optionally protected and a cycloalkyl group; and R², R¹⁰, R⁶³, R⁶⁴, R⁶⁵, R⁶⁶, R⁷³, R⁷⁴, Y⁷, Y⁸, Y⁹, m and --- are as defined above.

Preferable example of the optically active ester derivative of formula (IIb) is a compound represented by formula (IIb-1), (IIb-2) or (IIb-3):

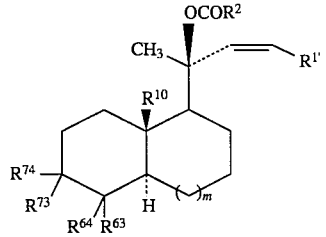
(IIb-1)

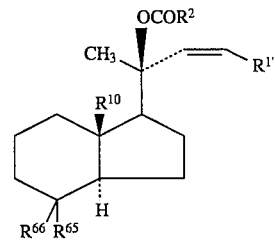
(IIb-2)

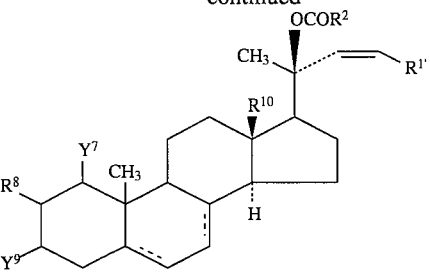
(IIb-3)

wherein R¹', R², R¹⁰, R⁶³, R⁶⁴, R⁶⁵, R⁶⁶, R⁷³, R⁷⁴, Y⁷, Y⁸, Y⁹, m and --- are as defined above.

Particularly preferable examples of the compounds (IIa) and (IIb) are as follows, besides those used in Examples described later:

3-hydroxycholesta-5,22E-dien-20-yl ester or a hydroxyl group-protected derivative thereof;

3-hydroxycholesta-5,22Z-dien-20-yl ester or a hydroxyl group-protected derivative thereof;

1,3-dihydroxycholesta-5,7,22E-trien-20-yl ester or a hydroxyl group-protected derivative thereof;

1,3-dihydroxycholesta-5,7,22Z-trien-20-yl ester or a hydroxyl group-protected derivative thereof;

1,3,25-trihydroxycholesta-5,7,22Z-trien-20-yl ester or a hydroxyl group-protected derivative thereof;

1,3,25-trihydroxycholesta-5,7,22E-trien-20-yl ester or a hydroxyl group-protected derivative thereof;

1,3,25-trihydroxyergosta-5,7,22Z-trien-20-yl ester or a hydroxyl group-protected derivative thereof;

24-epi-1,3,25-trihydroxyergosta-5,7,22Z-trien-20-yl ester or a hydroxyl group-protected derivative thereof;

1,3,25-trihydroxy-24,26,27-trihomocholesta-5,7,22E-trien-20-yl ester or a hydroxyl group-protected derivative thereof;

1,3,25-trihydroxy-24,26,27-trihomo-9,10-secocholesta-5,7,10(19),22E-tetraen-20-yl ester or a hydroxyl group-protected derivative thereof;

24-epi-1,3,25-trihydroxy-9,10-secoergosta-5,7,10(19),22Z-tetraen-20-yl ester or a hydroxyl group-protected derivative thereof;

1,3,25-trihydroxy-24,26,27-trihomo-9,10-secocholesta-5(10),6,8,22E-tetraen-20-yl ester or a hydroxyl group-protected derivative thereof;

1,3,25-trihydroxy-26-nor-26-methoxycarbonylcholesta-5,7,22Z-trien-20-yl ester or a hydroxyl group-protected derivative thereof;

1,3,24-trihydroxycholesta-5,7,22Z-trien-20-yl ester or a hydroxyl group-protected derivative thereof;

2-hydroxypropoxy-1,3,25-trihydroxycholesta-5,7,22Z-trien-20-yl ester or a hydroxyl group-protected derivative thereof;

1,3,25,26-tetrahydroxycholesta-5,7,22Z-trien-20-yl ester or a hydroxyl group-protected derivative thereof;

1,3,7,8,25-pentahydroxy-24,26,27-trihomo-9,10-secocholesta-5,10(19),22E-trien-20-yl ester or a hydroxyl group-protected derivative thereof;

2-(4-hydroxy-7a-methyl-2,3,3a,4,5,6,7,7a-octahydroinden-1-yl)-7-ethyl-7-hydroxy-5-nonen-2-yl ester or a hydroxyl group-protected derivative thereof;

2-(4-hydroxy-7a-methyl-2,3,3a,4,5,6,7,7a-octahydroinden-1-yl)-5,6-demthyl-3-hepten-2-yl ester or a hydroxyl group-protected derivative thereof;

3-hydroxy-9,10-seccoergosta-5,7,10(19),22E-tetraen-20-yl ester or a hydroxyl group-protected derivative thereof; and 2-(4-(2-(3-hydroxy-2-methylenebicyclo[3.1.0]-hexan-1-yl)-2-methoxyethylidene)-2,3,3a,4,5,6,7,7a-octahydro-7a-methylinden-1-yl)-5,6-dimethyl-3-hepten-2-yl ester or a hydroxyl group-protected derivative thereof.

The compound of formula (IIa) or (IIb) may be in the form of a Diels-Alder adduct with, for example, 4-phenyl-1,2,4-triazoline-3,5-dione, 1,4-dihydrophthalazine-1,4-dione, sulfur dioxide or the like The palladium salt, which is used as a catalyst when the compound of formula (IIa) or (IIb) is reacted with formic acid or a salt thereof, can be a per se known compound. There can be mentioned, for example, palladium acetylacetonate, palladium acetate, palladium chloride, palladium nitrate, bis(acetonitrile)palladium chloride, tris(dibenzylideneacetone)dipalladium chloroform. Of these, palladium acetate and palladium acetylacetonate are particularly preferable.

The tertiary phosphine, which is used in combination with the palladium salt, can also be a per se known compound such as a trialkylphosphine or a triarylphosphine. The carbon atoms of the alkyl portion of the trialkylphosphine are not particularly restricted but are generally 2–8 in view of the availability of such a trialkylphosphine. The alkyl portion may be straight-chain, branched chain or cyclic. Specific examples of such a trialkylphosphine are tributylphosphine, trihexylphosphine, trioctylphosphine and tricyclohexylphosphine. Specific example of the triarylphosphine is triphenylphosphine. Tributylphosphine is particularly preferable.

The proportion of the tertiary phosphine to the palladium salt is not particularly restricted and can be varied depending upon the kind of starting material used, etc. However, in general, the tertiary phosphine can be in an amount of about 0.5 to about 10 moles per gram atom of the palladium of the palladium salt. Use of the trialkylphosphine in an amount of 0.5–5 moles per gram atom of the palladium is preferable because the reaction can be conducted at low temperatures. Use of the triarylphosphine in an amount of 0.5–2 moles per gram atom of the palladium is preferable. Use of the tertiary phosphine in an amount of about 1–2 mole per gram atom of the palladium is convenient.

The palladium salt can be used in an amount of generally 0.0001–1 gram atom, preferably 0.001–0.3 gram atom, more preferably 0.01–0.1 gram atom in terms of palladium atom, per mole of the compound of formula (IIa) or (IIb).

The compound of formula (IIa) or (IIb) is reacted with formic acid or its salt. The formic acid salt is preferably a salt soluble in the organic solvent used in the reaction, and there can be mentioned, for example, ammonium salts of formic acid such as ammonium formate, triethylammonium formate, diisopropylethylammonium formate and the like.

The amount of formic acid or its salt used is not particularly restricted and can be varied depending upon the kind of the compound of formula (IIa) or (IIb), the kind of the catalyst, etc., but can be generally 1–10 moles, preferably 1–5 moles per mole of the compound of formula (IIa) or (IIb).

The reaction of the compound of formula (IIa) or (IIb) with formic acid or its salt can be conducted in the presence of a base, as necessary. The base is preferably a tertiary amine such as triethylamine, diisopropylethylamine, pyridine or the like. The amount of the base used is generally 0.01–10 moles, preferably 0.5–2 moles per mole of formic acid or its salt.

The reaction according to the present invention can be conducted at relatively low temperature owing to the use of the above-mentioned catalyst. It can be conducted generally at about −10° C. to about 40° C., preferably at about 0° C. to about 30° C. Depending upon the case, however, it can be conducted under heating up to the boiling point of the reaction solvent.

The reaction can be conducted in the presence of an organic solvent. As the organic solvent, there can be used, for example, hydrocarbons such as hexane, benzene and the like; ethers such as diethyl ether, tetrahydrofuran, dioxane and the like; acetonitrile, dimethylformamide; dimethyl sulfoxide; and chloroform. Of these, tetrahydrofuran, dioxane and benzene are preferable.

The optically active ester derivative of formula (IIa), which is used as a starting material in the above reaction, can be synthesized by esterifying a corresponding allyl alcohol [hereinafter referred to as allyl alcohol (a)]. This esterification can be conducted by an ordinary esterification reaction. The ester derivative of formula (IIa) can be obtained, for example, by reacting an alkali metal salt of an allyl alcohol (a) with a chloroformic acid ester or reacting. an allyl alcohol (a) with a chloroformic acid ester in the presence of a base such as pyridine or the like [Helv. Chim. Acta, Vol. 37, p.45 (1954)]. The allyl alcohol (a) can be obtained by reacting a corresponding carbonyl compound with an alkenyl metal such as 1-alkenyl lithium having an E-configuration. The allyl alcohol (a) can also be obtained by reacting a corresponding carbonyl compound with an alkynyl metal such as 1-alkynyl lithium, 1-alkynyl magnesium or the like to form an acetylene alcohol and reducing the actylene alcohol with lithium aluminum hydride.

Also, the optically active ester derivative of formula (IIb) can be synthesized from a corresponding allyl alcohol [hereinafter referred to as allyl alcohol (b)] by a process similar to the above. The allyl alcohol (b) can be obtained by reacting a corresponding carbonyl compound with an alkenyl metal such as 1-alkenyl lithium having a Z-configuration. The allyl alcohol (b) can also be obtained by reaction a corresponding carbonyl compound with an alkynl metal such as 1-alkynyl lithium, 1-alkynyl magnesium or the like to form an acetylene alcohol and reducing the actylene alcohol with a Lindlar catalyst, a diimide or the like.

According to the present process mentioned above, optically active olefins of formulas (Ia) and (Ib) can be produced from the optically active ester derivatives of formulas (IIa) and (IIb), respectively, at high yields at high selectivities.

The compound of formula (Ia) or (Ib) can be isolated from the reaction mixture and purified by a per se known method which generally used for isolation and purification of an organic compound from a reaction mixture containing the compound. For example, the reaction mixture containing the compound of formula (Ia) or (Ib) is poured into ice water; the resulting mixture is subjected to extraction with an organic solvent such as hexane, diethyl ether, ethyl acetate or the like; the extract is washed with cold diluted hydrochloric acid, an aqueous sodium hydrogencarbonate solution, an aqueous sodium chloride solution, etc. in this order, followed by drying and concentration to obtain a crude product; the crude product is as necessary purified by recrystallization, chromatography, etc., whereby an olefin of formula (Ia) or (Ib) can be obtained.

The reaction according to the present invention proceeds very stereospecifically. That is, when an ester derivative of formula (IIa) is used as a starting material, there is obtained an optically active olefin of formula (Ia) having the same steric configuration as the side chain of asteroid compound whose 20-position has a steric configuration reverse to that of natural steroid. When an ester derivative of formula (IIb) is used as a starting material, there is obtained an optically active olefin of formula (Ib) having the same steric configuration as the side chain of asteroid compound whose 20-position has a steric configuration same as that of natural steroid.

The thus obtained olefin of formula (Ia) or (Ib) has a physiological activity by itself and is useful as a medicine or as an intermediate for synthesis of physiologically active substances, particularly steroids. For example, (22E)-1,3,25-tris(t-butyldimethylsilyloxy)cholesta-5,7,22-triene and (22E)-1,3-bis(t-butyldimethylsilyloxy)-25-methoxymethoxycholesta-5,7,22-triene can be converted to 22,23-dehydro-1,25-dihydroxyvitamin $D_3$ having a strong vitamin D activity, by being subjected to photoisomerization, thermal isomerization and deprotection by an ordinary method used in the synthesis of vitamin D derivatives.

The present invention is hereinafter described more specifically by way of Examples. However, the Examples are merely for illustration and not for restriction of the present invention.

Reference Example 1

2.35 ml of 1.5M pentane solution of t-butyl lithium was dropwise added to a solution of 606 mg of (Z)-5-iodo-4-penten-1-yl t-butyldimethylsilyl ether dissolved in 5 ml of diethyl ether, at −78° C. in 9 minutes in an argon atmosphere. The reaction mixture was stirred at the same temperature for 2 hours. Thereto was dropwise added, in 5 minutes, a solution of 640 mg of 3-(t-butyldimethylsilyloxy)pregn-5-en-20-one dissolved in 10 ml of tetrahydrofuran. The reaction mixture was warmed to room temperature in 1 hour, then mixed with water and subjected to extraction with ethyl acetate. The extract was water-washed, dried over anhydrous magnesium sulfate, and concentrated under reduced pressure. The residue was dissolved in a mixed solution consisting of 8 ml of ethanol and 3 ml of tetrahydrofuran. To the solution was added 75 mg of sodium borohydride, and the mixture was stirred at room temperature for 1.5 hours to reduce unreacted 3-(t-butyldimethylsilyloxy)pregn-5-en-20-one. The reaction mixture was mixed with water and subjected to extraction with ethyl acetate. The extract was water-washed, dried over anhydrous magnesium sulfate and concentrated under reduced pressure. The residue was purified by silica gel column chromatography to obtain 706.5 mg (yield: 75%) of (22Z)-3,26-di(t-butyldimethylsilyloxy)-27-norcholesta-5,22-dien-20-ol.

Reference Example 2

In 7 ml of tetrahydrofuran was dissolved 706.5 mg of the (22Z)-3,26-di(t-butyldimethylsilyloxy)-27-norcholesta-5,22-dien-20-ol obtained in Reference Example 1. To the solution was dropwise added, at −78° C., 0.9 ml of 1.5M pentane solution of t-butyl lithium. The reaction mixture was stirred at the same temperature for 30 minutes. Thereto was dropwise added 0.13 ml of methyl chloroformate. The mixture was stirred at room temperature for 15 hours. The reaction mixture was mixed with an aqueous sodium hydrogencarbonate solution and subjected to extraction with ethyl acetate. The extract was washed with an aqueous sodium hydrogencarbonate solution, dried over anhydrous magnesium sulfate and concentrated under reduced pressure to obtain 782.6 mg of (22Z)-3,26-di(t-butyldimethylsilyloxy)-27-norcholesta-5,22-dien-20-yl methyl carbonate as white crystals.

Reference Example 3

Reactions, separation and purification were conducted in the same manner as in Reference Example 1 except that the (Z)-5-iodo-4-penten-1-yl t-butyldimethylsilyl ether used in Reference Example 1 was replaced by (E)-5-iodo-4-penten-1-yl t-butyldimethylsiliy ether, to obtain 939 mg of (22E)-3,26-di(t-butyldimethylsilyloxy)-27-norcholesta-5,22-dien-20-ol.

Reference Example 4

In 8 ml of tetrahydrofuran was dissolved 939 mg of the (22E)-3,26-di(t-butyldimethylsilyloxy)-27-norcholesta-5,22-dien-20-ol obtained in Reference Example 3. To the solution was dropwise added 1.2 ml of 1.5M pentane solution of t-butyl lithium at −83° C. in 5 minutes. The reaction mixture was stirred at the same temperature for 30 minutes. Thereto was dropwise added 0.17 ml of methyl chloroformate, and the mixture was stirred overnight at room temperature. The reaction mixture was mixed with an aqueous sodium hydrogencarbonate solution and subjected to extraction with ethyl acetate. The extract was washed with an aqueous sodium hydrogencarbonate solution, dried over anhydrous magnesium sulfate and concentrated under reduced pressure to obtain (22E)-3,26-di(t-butyldimethylsilyloxy)-27-norcholesta-5,22-dien-20-yl methyl carbonate.

Reference Example 5

0.32 ml of 1.6M hexane solution of butyl lithium was dropwise added to a solution of 120 mg of 5-ethyl-5-methoxymethoxy-1-heptyne dissolved in 4 ml of tetrahydrofuran, at −78° C. in a nitrogen atmosphere. The reaction mixture was stirred at the same temperature for 30 minutes. Thereto was dropwise added a solution of 112 mg of 4-benzoyloxy-7a-methyl-2,3,3a,4,5,6,7,7a-octahydroinden-1-yl-ethanone dissolved in 3 ml of tetrahydrofuran. The reaction mixture was warmed to 0° C. and mixed with an aqueous ammonium chloride solution. The mixture was subjected to extraction with diethyl ether. The extract was washed with a saturated aqueous sodium chloride solution, dried over anhydrous magnesium sulfate and concentrated under reduced pressure. The residue was purified by silica gel column chromatography to obtain 97 mg of 2-(4-benzoyloxy-7a-methyl-2,3,3a,4,5,6,7,7a-octahydroinden-1-yl)-7-ethyl-7-methoxymethoxy-3-nonyn-2-ol having the following properties.

NMR spectrum (270 MHz, $CDCL_3$) δ0.83 (6H,t,J=7.6 Hz), 1.33 (3H,s), 1.47 (3H,s), 3.37 (3H,s), 4.65 (2H,s), 5.43 (1H,s), 7.43 (2H,t,J=7 Hz), 7.55 (1H,q,J=7 Hz), 8.08 (2H, d,J=7 Hz)

Reference Example 6

97 mg of 2-(4-benzoyloxy-7a-methyl-2,3,3a,4,5,6,7,7a-octahydroinden-1-yl)-7-ethyl-7-methoxymethoxy-3-nonyn-2-ol obtained in Reference Example 5 was dissolved in 2 ml of tetrahydrofuran. The solution was dropwise added, at room temperature, to a suspension of 120 mg of lithium aluminum hydride in 3 ml of tetrahydrofuran. The mixture was refluxed for 30 minutes. The reaction mixture was cooled and then diluted with diethyl ether. The mixture was poured into an aqueous solution containing ammonium chloride and sodium hydroxide. The resulting mixture was subjected to extraction with diethyl ether. The extract was washed with a saturated aqueous sodium chloride solution, dried over anhydrous magnesium sulfate and concentrated under reduced pressure. The residue was purified by silica gel column chromatography to obtain 40 mg of 2-(4-hydroxy-7a-methyl-2,3,3a,4,5,6,7,7a-octahydroinden-1-yl)-7-ethyl-7-methoxymethoxy-3E-nonen-2-ol having the following properties.

NMR spectrum (270 MHz, CDCL$_3$) δ0.84 (6H,t,J=7.6 Hz), 1.10 (3H,s), 1.32 (3H,s), 3.40 (3H,s), 4.09 (1H,br.s), 4.66 (2H,s), 5.46–5.64 (2H,m)

Reference Example 7

20 mg of 2-(4-hydroxy-7a-methyl-2,3,3a,4,5,6,7,7a-octahydroinden-1-yl)-7-ethyl-7-methoxymethoxy-3E-nonen-2-ol obtained in Reference Example 6 was dissolved in 4 ml of tetrahydrofuran. To the solution was dropwise added, −78° C., 0.08 ml of 1.6M hexane solution of n-butyl lithium. The reaction mixture was stirred at the same temperature for 10 minutes. Thereto was dropwise added 0.013 ml of methyl chloroformate. The mixture was stirred at room temperature for 15 hours. The reaction mixture was mixed with an aqueous sodium hydrogencarbonate solution, followed by extraction with ethyl acetate. The extract was washed with an aqueous sodium hydrogencarbonate solution, dried over anhydrous magnesium sulfate and concentrated under reduced pressure to obtain 26 mg of 2-(4-methoxycarbonyloxy-7a-methyl-2,3,3a,4,5,6,7,7a-octahydroinden-1-yl)-7-ethyl-7-methoxymethoxy-3E-nonen-2-yl methyl carbonate.

Reference Example 8

733.9 mg of trans-1-iodo-4-(1-ethoxyethoxy)-4-methyl-1-pentene was dissolved in 7 ml of diethyl ether. To the solution was dropwise added 2.9 ml of 1.6M pentane solution of t-butyl lithium at −80° C. in a nitrogen atmosphere. The reaction mixture was stirred at the same temperature for 2 hours. Thereto was dropwise added a solution of 430 mg of 3-(t-butyldimethylsilyloxy)pregna-5-en-20-one dissolved in 9 ml of tetrahydrofuran. The mixture was stirred for 20 minutes. The reaction mixture was heated to room temperature. Thereto was added water, followed by extraction with ethyl acetate. The react was washed with a saturated aqueous sodium chloride solution, dried over anhydrous sodium sulfate and concentrated under reduced pressure. The residue was purified by silica gel column chromatography to obtain 291 mg of 25-(1-ethoxyethyoxy)-3-(t-butyldimethylsilyloxy)cholesta-5,22E-dien-20-ol.

Reference Example 9

291.7 mg of 25-(1-ethoxyethoxy)-3-(t-butyldimethylsilyloxy)cholesta-5,22E-dien-20-ol was dissolved in 5 ml of tetrahydrofuran. To the solution was dropwise added 0.38 ml of 1.6M pentane solution of t-butyl lithium at −80° C. in a nitrogen atmosphere. The reaction mixture was stirred at the same temperature for 30 minutes. Thereto was added 0.06 ml of methyl chloroformate. The mixture was stirred for 14 hours. The reaction mixture was warmed to room temperature and mixed with an aqueous sodium hydrogencarbonate solution. The mixture was subjected to extraction with ethyl acetate. The extract was dried over anhydrous sodium sulfate and concentrated under reduced pressure to obtain 320 mg of 25-(1-ethoxyethyoxy)-3-(t-butyldimethylsilyloxy)cholesta-5,22E-dien-20-yl methyl carbonate.

Reference Example 10

Reactions, separation and purification were conducted in the same manner as in Reference Example 8 except that the trans-1-iodo-4-(1-ethoxyethoxy)-4-methyl-1-pentene used in Reference Example 8 was replaced by cis-1-iodo-4-(1-ethoxyethoxy)-4-methyl-1-pentene, to obtain 468 mg of 25-(1-ethoxyethyoxy)-3-(t-butyldimethyl-silyloxy)cholesta-5,22Z-dien-20-ol.

Reference Example 11

Reactions, separation and purification were conducted in the same manner as in Reference Example 9 except that 291.7 mg of the 25-(1-ethoxyethoxy)-3-(t-butyldimethylsilyloxy)cholesta-5,22E-dien-20-ol used in Reference Example 9 was replaced by 634 mg of 25-(1-ethoxyethoxy)-3-(t-butyldimethylsilyloxy)cholesta-5,22Z-dien-20-ol, to obtain 695 mg of 25-(1-ethoxyethyoxy)-3-(t-butyldimethyl-silyloxy)cholesta-5,22Z-dien-20-yl methyl carbonate.

Reference Example 12

Reactions, separation and purification were conducted in the same manner as in Reference Example 8 except that the trans-1-iodo-4-(1-ethoxyethoxy)-4-methyl-1-pentene used in Reference Example 8 was replaced by cis-1-iodo-4-(1-methoxymethoxy)-4-methyl-1-pentene, to obtain 304 mg of 25-(1-methoxymethyoxy)-3-(t-butyldimethylsilyloxy)cholesta-5,22Z-dien-20-ol.

Reference Example 13

Reactions, separation and purification were conducted in the same manner as in Reference Example 9 except that the 25-(1-ethoxyethoxy)-3-(t-butyldimethylsilyloxy)cholesta-5,22E-dien-20-ol used in Reference Example 9 was replaced by 634 mg of 25-(1-methoxymethoxy)-3-(t-butyldimethylsilyloxy)cholesta-5,22Z-dien-20-ol, to obtain 359.4 mg of 25-(1-methoxymethyoxy)-3-(t-butyldimethylsilyloxy)cholesta-5,22Z-dien-20-yl methyl carbonate.

EXAMPLE 1

30.4 mg of palladium acetylacetonate and 0.025 ml of tributylphosphine were mixed in 2 ml of benzene in an argon atmosphere to prepare a yellow solution of a palladium catalyst. To this catalyst solution was added 2.5 ml of 1.0M benzene solution of triethylammonium formate. Thereto was further added a solution of 344 mg of (20S,22Z)-3,26-di(t-butyldimethylsilyloxy)-27-norcholesta-5,22-dien-20-yl methyl carbonate (obtained in Reference Example 2) dissolved in 2 ml of benzene. The mixture was stirred at room temperature for 45 minutes. The reaction mixture was diluted with hexane, then water-washed, dried over anhydrous magnesium sulfate and filtered through Florisil. The filtrate was concentrated under reduced pressure to obtain 240.7 mg of (20R,22E)-3,26-di(t-butyldimethylsilyloxy)-27-norcholesta-5,22-diene having the following properties, as white crystals.

NMR spectrum (400 MHz, CDCL$_3$) δ0.04 (6H,s), 0.05 (6H,s), 0.68 (3H,s), 0.89 (18H,s), 1.00 (18H,s), 1.00 (3H,d, J=6.5 Hz), 0.88–2.31 (25H,m), 3.47 (1H,t,t,J=5.0 Hz), 3.59 (2H,t,J=6.6 Hz), 5.24–5.34 (3H,m)

EXAMPLE 2

Reactions, separation and purification were conducted in the same manner as in Example 1 except that 2.5 ml of the 1.0M benzene solution of triethylammonium formate used in Example 1 was replaced by 1.0 ml of 1.0M benzene solution of triethylammonium formate, to obtain 294.2 mg of (20R,22E)-3,26-di(t-butyldimethylsilyloxy)-27-norcholesta-5,22-diene.

294.2 mg of the (20R,22E)-3,26-di(t-butyldimethylsilyloxy)-27-norcholesta-5,22-diene obtained above was dissolved in 5 ml of tetrahydrofuran. To the solution was added 2.40 ml of 1M tetrahydrofuran solution of tetrabutylammonoium fluoride. The mixture was stirred at room temperature for 15 hours. The reaction mixture was diluted with methylene chloride, followed by water washing. The aqueous layer was subjected to extraction with methylene chloride and chloroform. The organic layer was dried over anhydrous magnesium sulfate. The solvent was removed by distillation. The residue was washed with hot hexane, and the resulting solid was recrystallized from chloroform to obtain 126.6 mg of (20R,22E)-27-norcholesta-5,22-diene-3,26-diol having the following properties, as white crystals. The mother liquor of recrystallization was concentrated and recrystallized from chloroform to obtain 18.9 mg of (20R,22E)-27-norcholesta-5,22-diene-3,26-diol was crystals.

NMR spectrum (400 MHz, $CDCL_3$) $\delta 0.64$ (3H,s), 0.88 (3H,d,J=6.6 Hz), 0.98 (3H,s), 0.89–2.30 (27H,m), 3.50 (1H,m), 3.64 (2H,t,J=6.6 Hz), 5.29–5.34 (3H,m)

EXAMPLE 3

30.4 mg of palladium acetylacetonate and 0.025 ml of tributylphosphine were mixed in 2 ml of benzene in an argon atmosphere to prepare a yellow solution of a palladium catalyst. To the catalyst solution was added 5 ml of 1.0M benzene solution of triethylammonium formate. Thereto was added a solution obtained by dissolving, in 9 ml of benzene, 688 mg of the (20S,22E)-3,26-di(t-butyldimethylsilyloxy)-27-norcholesta-5,22-dien-20-yl methyl carbonate obtained in Reference Example 4. The mixture was stirred at room temperature for 3 hours. The reaction mixture was diluted with hexane, followed by water washing, drying over anhydrous magnesium sulfate and filtration through Florisil. The filtrate was concentrated under reduced pressure to obtain 568.7 mg of (20S,22E)-3,26-di(t-butyldimethylsilyloxy)-27-norcholesta-5,22-diene having the following properties, as white crystals.

NMR spectrum (400 MHz, $CDCL_3$) $\delta 0.05$ (12H,s), 0.64 (3H,s), 0.88–0.90 (21H,s ×3), 0.98 (3H,m), 0.89–2.26 (25H, m), 3.47 (1H,m), 3.60 (2H,t,J=6.6 Hz), 5.22–5.30 (3H,m)

EXAMPLE 4

30.4 mg of palladium acetylacetonate and 0.025 ml of tributylphosphine were mixed in 2 ml of benzene in an argon atmosphere to prepare a yellow solution of a palladium catalyst. To the catalyst solution was added 5 ml of 1.0M benzene solution of triethylammonium formate. 2 ml of the mixture was taken and mixed with a solution obtained by dissolving, in 2 ml of benzene, 26 mg of the (2S)-2-(4-methoxycarbonyloxy-7a-methyl-2,3,3a,4,5,6,7,7a-octahydroinden-1-yl)-7-ethyl-7-methoxymethoxy-3E-nonen-2-yl methyl carbonate obtained in Reference Example 7. The mixture was stirred at room temperature for 1 hour. The reaction mixture was diluted with hexane, followed by water washing, drying over anhydrous magnesium sulfate and filtration through Florisil. The filtrate was concentrated under reduced pressure to obtain 20 mg of (2S)-2-(4-methoxycarbonyloxy-7a-methyl-2,3,3a,4,5,6,7,7a-octahydroinden-1-yl)-7-ethyl-7-methoxymethoxy-3E-nonen having the following properties.

NMR spectrum (270 MHz, $CDCL_3$) $\delta 0.83$ (6H,t,J=7 Hz), 0.89 (3H,d,J=7 Hz), 1.26 (3H,s), 3.40 (3H,s), 3.76 (3H,s), 4.66 (2H,s), 5.0 (1H,br.s), 5.16–5.39 (2H,m)

EXAMPLE 5

29.2 mg of palladium acetylacetonate and 0.024 ml of tributylphosphine were mixed in 1 ml of benzene in an argon atmosphere to prepare a yellow solution of a palladium catalyst. To the catalyst solution was added a mixture of 2.5 mM of formic acid and 2.4 mM of triethylamine. There was further added a solution obtained by dissolving, in 2 ml of benzene, 314 mg of the (20S)-25-(1-ethoxyethyoxy)-3-(t-butyldimethylsilyloxy)cholesta-5,22E-dien-20-yl methyl carbonate obtained in Reference Example 9. The mixture was stirred at room temperature for 45 minutes. The reaction mixture was diluted with 40 ml of hexane, followed by water washing, drying over anhydrous magnesium sulfate and concentration under reduced pressure to obtain 210 mg (yield: 75%) of (20S)-25-(1-ethoxyethoxy)-3-(t-butyldimethylsilyloxy)cholesta-5,22E-diene.

The above obtained 25-(1-ethoxyethyoxy)-3-(t-butyldimethylsilyloxy)cholesta-5,22E-diene was dissolved in 20 ml of methanol. To solution was added 3 mg of pyridinium p-toluenesulfonate. The mixture was stirred at room temperature for 3 hours. An aqueous sodium hydrogencarbonate solution was added to the reaction mixture, followed by extraction with ethyl acetate. The extract was dried over anhydrous magnesium sulfate and concentrated under reduced pressure to obtain (20S)-cholesta-5,22E-diene-3,25-diol.

Melting point: 205°–205.5° C.

$^1$H-NMR spectrum ($CDCL_3$) $\delta 0.66$ (s,3H), 0.92 (d,J=6.60 Hz,3H), 0.99 (s,3H), 1.201 (s,3H), 1.204 (s,3H), 3.46–3.55 (m, 1H), 5.31–5.46 (m,3H) $^{13}$C-NMR spectrum ($CDCL_3$) $\delta 12.1$, 19.4, 20.8, 21.7, 24.1, 27.9, 31.7, 31.8, 31.9, 36.5, 37.2, 39.2, 40.4, 42.3, 42.4, 47.0, 50.2, 56.1, 56.6, 70.7, 71.8, 21.6, 122.5, 140.8, 141.9

EXAMPLE 6

64 mg of palladium acetylacetonate and 0.052 ml of tributylphosphine were mixed in 4.5 ml of benzene in an argon atmosphere to prepare a yellow solution of a palladium catalyst. To the catalyst solution was added a mixture of 2.1 m mol of formic acid and 2.1 m mol of triethylamine. There was further added a solution obtained obtained by dissolving, in 2 ml of benzene, 695 mg of the (20S)-25-(1-ethoxyethoxy)-B-(t-butyldimethylsilyloxy)cholesta-5,22Z-dien-20-yl methyl carbonate obtained in Reference Example 11. The mixture was stirred at room temperature for 1.5 hours. The reaction mixture was diluted with 40 ml of hexane, followed by water washing, drying over anhydrous magnesium sulfate and concentration under reduced pressure to obtain (20R)-25-(1-ethoxyethoxy)-3-(t-butyldimethylsilyloxy)cholesta-5,22E-diene.

The above obtained (20R)-25-(1-ethoxyethoxy)-3-(t-butyldimethylsilyloxy)cholesta-5,22E-diene was dissolved in 20 ml of methanol. To the solution was added 3 mg of pyridinium p-toluenesulfonate. The mixture was stirred at room temperature for 3 hours. An aqueous sodium hydrogencarbonate solution was added to the reaction mixture, followed by extraction with ethyl acetate. The extract was dried over anhydrous magnesium sulfate and concentrated under reduced pressure to obtain 376 mg of (20R)-cholesta-5,22E-diene-3,25-diol.

Melting point: 180°–180.5° C.

$^1$H-NMR spectrum ($CDCL_3$) $\delta 0.70$ (s,3H), 1.00 (s,3H), 1.03 (d,J=6.59 Hz,3H), 1.19 (s,3H), 3.46–3.57 (m,]H), 5.31–5.43 (m,3H)

13C-NMR spectrum (CDCL₃) δ2.1, 19.4, 20.7, 21.1, 24.3, 28.8, 29.0, 31.6, 31.9, 36.5, 37.2, 39.7, 40.3, 42.3, 46.8, 50.1, 55.6, 56.8, 0.5, 71.8, 21.6, 122.5, 140.7,

EXAMPLE 7

38.1 mg of palladium acetylacetonate and 0.003 ml of tributylphosphine were mixed in 3 ml of benzene in an argon atmosphere to prepare a yellow solution of a palladium catalyst. To the solution was added a mixture of 1.25 m mol of formic acid and 1.25 m mol of triethylamine. There was further added a solution obtained obtained by dissolving, in 2 ml of benzene, 359 mg of the (20S)-25-(1-methoxymethoxy)-3-(t-butyldimethylsilyloxy)cholesta-5,22Z-dien-20-yl methyl carbonate obtained in Reference Example 13. The mixture was stirred at room temperature for 2.5 hours. The reaction mixture was diluted with 40 ml of hexane, followed by water washing, drying over anhydrous magnesium sulfate and concentration under reduced pressure to obtain (20R)-25-(1-methoxymethoxy)-3-(t-butyldimethylsilyloxy)cholesta-5,22E-diene.

The above obtained (20R)-25-(1-methoxymethoxy)-3-(t-butyldimethylsilyloxy)cholesta-5,22E-diene was dissolved in 3 ml of acetic acid. To the solution was added 0.2 mg of 2N sulfic acid. The mixture was stirred at room temperature for 3 hours. The reaction mixture was put into water, followed by extraction with ethyl acetate. The extract was washed, dried over anhydrous magnesium sulfate and concentrated under reduced pressure to obtain (20R)-3-(t-butyldimethylsilyloxy)cholesta-5,22E-dien-25-ol.

The above obtained (20R)-3-(t-butyldimethylsilyloxy)cholesta-5,22E-dien-25-ol was dissolved in 10 ml of tetrahydrofuran. To the solution was added 1.5 mg of tetrahydrofuran solution of 1M of tetrabutylammonium fluoride. The mixture was stirred at room temperature for 2 hours. The reaction mixture was diluted with methylene chloride, followed by water washing, drying over anhydrous magnesium sulfate and concentrated under reduced pressure to obtain 250 mg of (20R)-cholesta-5,22E-diene-3,25-diol.

Reference Example 13

2.3 ml of 1.5M pentene solution of t-butyllithum was dropwise added, at −78° C., to a solution 416 mg of (E)-3,4-dimethyl-1-iodo-1-pentene dissolved in 5 ml of diethyl ether. The reaction mixture was stirred at room temperature for 2 hours. Thereto was dropwise added a solution of 682 mg of 1-acetyl-4-(2-(3-(t-butyldimethylsilyloxy)-2-methylenebicyclo[3.1.0]hexane-1-yl)-2-methoxyethylidene)-2,3,3a,4,5,6,7,7a-octahydro-7a-methylindene dissolved in 10 ml of tetrahydrofuran. The mixture was stirred for 1 hour. Thereto was dropwise added 0.3 ml of methyl chloroformate. The mixture was stirred at room temperature overnight. The reaction mixture was mixed with an aqueous sodium hydrogencarbonate solution, followed by extraction with ethyl acetate. The extract was washed with an aqueous sodium hydrogencarbonate solution and concentrated under reduced pressure to obtain 1.04 g (2S, 3E)-5,6-dimethyl-2-(4-(2-(3-(t-butyldimethylsilyloxy)-2-methylenebicyclo[3.1.0]hexane-1-yl)-2-methoxyethylidene)-2,3,3a,4,5,6,7,7a-octahydro-7a-methylinden-1-yl)-2-methoxycarbonyloxy-3-heptene having the follow property.

FD mass spectrum [M]⁺ 540

EXAMPLE 8

0.1 mM of palladium acetate and 0.1 mM of tributylphosphine were mixed in 3 ml of benzene in an argon atmosphere to prepare a yellow solution of a palladium catalyst. To the solution was added a solution of 5 mM of formic acid and 5 mM of triethylamine dissolved in 5 ml of benzene. There was further added 614 mg (1 mM) of (2S,3E)-5,6-dimethyl-2-(4-(2-(3-(t-butyldimethylsilyloxy)-2-methylenebicyclo [3.1.0]hexane-1-yl)-2-methoxyethylidene-2,3,3a,4,5,6,7,7a-octahydro-7a-methylinden-1-yl)-2-methoxycarbonyloxy-3-heptene. The mixture was stirred at room temperature for 3 hours. The reaction mixture was diluted with 40 ml of water, followed by extraction with pentane. The extract was dried and concentrated. The residue was purified by silica gel column chromatography to obtain 464 mg (yield: 86%) of (2S)-5,6-dimethyl-2-(4-(2-(3-(t-butyldimethylsilyloxy)-2-methyl-enebicyclo[3.1.0]hexane-1-yl)-2-methoxyethyl-idene)-2,3,3a,4,5,6,7,7a-octahydro-7a-methylinden-1-yl)-3-heptene having the follow property.

FD mass spectrum [M]⁺ 540

We claim:

1. A process for producing an optically active olefin represented by general formula (Ib)

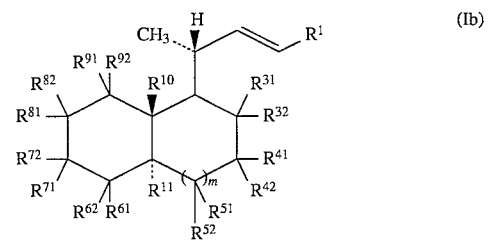

wherein $R^1$ represents an alkyl or alkenyl group which may be substituted by an optionally protected hydroxyl group, an optionally protected oxo group, an optionally protected carboxyl group or a halogen atom;

$R^{10}$ represents a lower alkyl group;

$R^{11}$ represents a hydrogen atom or a lower alkyl group;

each of $R^{31}$, $R^{32}$, $R^{41}$, $R^{42}$, $R^{51}$, $R^{52}$, $R^{61}$, $R^{62}$, $R^{71}$, $R^{72}$, $R^{81}$, $R^{82}$, $R^{91}$ and $R^{92}$ represents a hydrogen atom, an optionally protected hydroxyl group, or an organic group selected from an alkyl, alkenyl, cycloalkyl, cycloalkylidenealkyl, cycloalkenylalkenyl, cycloalkenyl, aryl or aralkyl group which may be substituted by an optionally protected hydroxyl group, an optionally protected oxo group, an optionally protected carboxyl group, cyano group, an optionally substituted amino group or a halogen atom, or each one pair of the substituents on two adjacent carbon atoms, that is, ($R^{31}$ or $R^{32}$) and ($R^{41}$ or $R^{42}$); ($R^{41}$ or $R^{42}$) and ($R^{51}$ or $R^{52}$); ($R^{51}$ or $R^{52}$) and $R^{11}$; $R^{11}$ and ($R^{61}$ or $R^{62}$); ($R^{61}$ or $R^{62}$) and ($R^{71}$ or $R^{72}$); ($R^{71}$ or $R^{72}$) and ($R^{81}$ or $R^{82}$); and ($R^{81}$ or $R^{82}$) and ($R^{91}$ or $R^{92}$), may be bonded to each other to form an additional carbon-to-carbon bond, or each one pair of the substituents on the same carbon atom, that is, $R^{31}$ and $R^{32}$; $R^{41}$ and $R^{42}$; $R^{51}$ and $R^{52}$; $R^{61}$ and $R^{62}$; $R^{71}$ and $R^{72}$; $R^{81}$ and $R^{82}$; $R^{91}$ and $R^{92}$, may be bonded to each other to form an optionally protected oxo group or a group of the formula

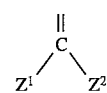

wherein each of $Z^1$ and $Z^2$ represents a hydrogen atom or an organic group as described for $R^{31}$ to $R^{91}$, or $R^{61}$, $R^{62}$, $R^{71}$ and $R^{72}$ may form an additional ring together with the carbon atoms to which they are bonded; and m is 0 or 1, which process comprises reacting an optically active ester derivative represented by the general formula (IIb)

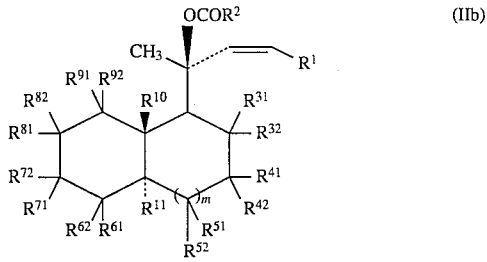

wherein $R^1$, $R^{10}$, $R^{11}$, $R^{31}$, $R^{32}$, $R^{41}$, $R^{42}$, $R^{51}$, $R^{52}$, $R^{61}$, $R^{62}$, $R^{71}$, $R^{72}$, $R^{81}$, $R^{82}$, $R^{91}$, $R^{92}$ and m are as defined above and $R^2$ represents a hydrogen atom, an alkoxy group, an alkenyloxy group or an aralkyloxy group of which the aryl moiety may be substituted by a halogen atom, a nitro group, a lower alkyl group or a lower alkoxy group with formic acid or a salt thereof in the presence of a catalyst comprising a palladium salt and a tertiary phosphine and wherein, in the aforementioned definitions, the optionally protected hydroxyl group is a hydroxyl group which may optionally be protected by an acyl group, an alkoxycarbonyl group, a tri-substituted silyl group, a 1-alkoxyalkyl group or a 2-oxacycloalkyl group;

the optionally substituted amino group is selected from the group consisting of amino, methylamino, dimethylamino, acetylamino, benzyloxy-carbonylamino, t-butoxycarbonylamino, benzyloxyamino and p-toluenesulfonylamino;

the optionally protected oxo group is an oxo group which may optionally be protected by an acyclic ketal, a cyclic ketal, an acyclic thioketal or a cyclic thioketal; and, the optionally protected carboxyl group is selected from the group consisting of a carboxyl group, lower alkoxycarbonyl groups and aralkyloxycarbonyl groups.

2. The process according to claim 1, wherein the palladium salt is palladium acetate or palladium acetylacetonate.

3. The process according to claim 1, wherein the tertiary phosphine is tributylphosphine.

4. The process according to claim 1, wherein the tertiary phosphine is used an amount of 0.5–5 moles per gram atom of the palladium of the palladium salt.

5. The process according to claim 4, wherein the tertiary phosphine is used an amount of 1–2 mole per gram atom of the palladium of the palladium salt.

6. The process according to claim 1, wherein the palladium salt is used an amount of 0.0001–1 gram atom in terms of palladium atom, per mole of the compound of formula (IIa) or (IIb).

7. The process according to claim 1, wherein the reaction is conducted at a temperature ranging from about −10° C. to about 40° C.

8. The process according to claim 7, wherein the reaction is conducted at a temperature ranging from about 0° C. to about 30° C.

9. A process according to claim 1, wherein the optically active ester derivative is a compound represented by formula (IIb-1)

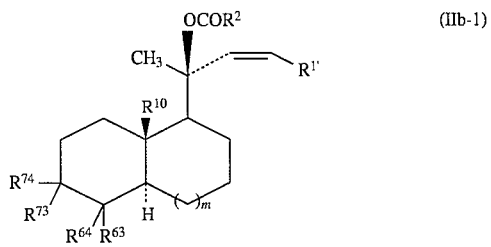

wherein $R_{1'}$ represents a straight-chain or branched-chain alkyl group which may be optionally substituted by one or two groups selected from the group consisting of a hydroxyl group which may be optionally protected, an oxo group which may be optionally protected, a carboxyl group which may be optionally protected and a cycloalkyl group;

one of $R^{63}$, $R^{64}$, $R^{73}$ and $R^{74}$ represents a hydroxyl group which may be optionally protected or a group of formula (a)

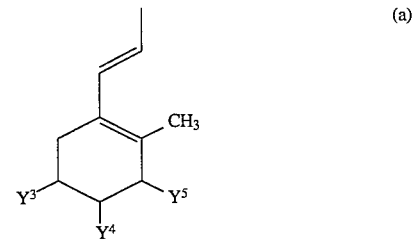

in which $Y^3$ represents a hydroxyl group which may be optionally protected; $Y^4$ represents a hydrogen atom, a fluorine atom or a lower alkoxy group which may be substituted by a hydroxyl group which may be optionally protected; and $Y^5$ represents a hydrogen atom or a hydroxyl group which may be optionally protected, and each of the remaining groups is a hydrogen atom or the remaining two groups on two adjacent carbon atoms are bonded to each other to form an additional carbon-to-carbon bond, or $R^{63}$ and $R^{64}$ are bonded to each other to form an oxo group which may be optionally protected or a group represented by formula (b), (c), (d) or (e)

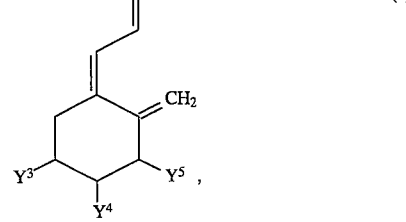

23
-continued (d)
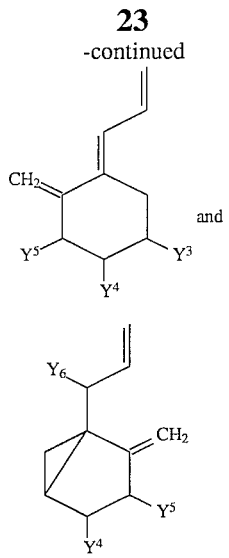

and (e)

Y³, Y⁴ and R⁵ are as defined above and Y⁶ represents a lower alkoxy group and R⁷³ and R⁷⁴ each represent a hydrogen atom, or R⁶³, R⁶⁴, R⁷³ and R⁷⁴ constitute the A and B rings portion of steroid together with the carbon atoms to which they are bonded; and R², R¹⁰ and m are as defined in claim 1.

10. A process according to claim 9, wherein the optically active ester derivative is a compound represented by formula (IIb-2)

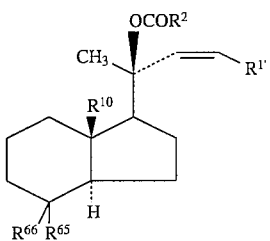

(IIb-2)

24 wherein one of R⁶⁵ and R⁶⁶ is a hydroxyl group which may be optionally protected and the other is a hydrogen atom, or R⁶⁵ and R⁶⁶ are bonded to each other to form an oxo group which may be protected or a group of formula (b), (c), (d) or (e) mentioned in claim 9;

R¹' is as defined in claim 9; and

R² and R¹⁰ are as defined in claim 1.

11. A process according to claim 9; wherein the optically active ester derivative is a compound represented by formula (IIb-3)

(IIb-3)

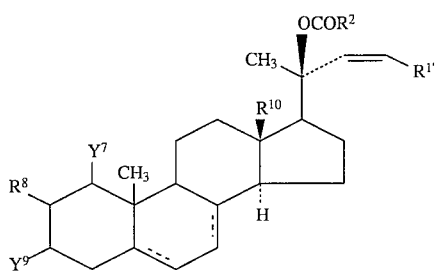

wherein Y⁷ and Y⁹ each represent a hydrogen atom or a hydroxyl group which may be optionally protected;

Y⁸ represents a hydrogen atom, a fluorine atom or a lower alkoxy group which may be substituted by a hydroxyl group which may be optionally protected;

--- represents a single or double bond;

R¹' is as defined in claim 9; and

R² and R¹⁰ are as defined in claim 1.

* * * * *